United States Patent [19]

Hänssler et al.

[11] Patent Number: 5,696,150
[45] Date of Patent: Dec. 9, 1997

[54] FUNGICIDAL ACTIVE COMPOUND COMBINATIONS

[75] Inventors: Gerd Hänssler, Leverkusen; Stefan Dutzmann, Hilden; Matthias Wunsch, Langenfeld, all of Germany

[73] Assignee: Bayer Aktiengesellschaft, Leverkusen, Germany

[21] Appl. No.: 713,387

[22] Filed: Sep. 13, 1996

[30] Foreign Application Priority Data

Sep. 21, 1995 [DE] Germany ................. 195 35 064.2
Dec. 20, 1995 [DE] Germany ................. 195 47 627.1

[51] Int. Cl.$^6$ ............... A01N 37/18; A01N 43/36
[52] U.S. Cl. ............ 514/422; 514/427; 514/624
[58] Field of Search ............... 514/427, 422, 514/624

[56] References Cited

U.S. PATENT DOCUMENTS

| | | | |
|---|---|---|---|
| 3,912,752 | 10/1975 | Meiser et al. | 260/308 R |
| 3,952,002 | 4/1976 | Kramer et al. | 260/308 R |
| 3,991,071 | 11/1976 | Brookes et al. | 260/309 |
| 4,080,462 | 3/1978 | Brookes et al. | 424/273 R |
| 4,780,551 | 10/1988 | Nyfeler et al. | 549/422 |
| 4,988,734 | 1/1991 | Kraatz et al. | 514/624 |
| 5,112,849 | 5/1992 | Staub et al. | 514/427 |

FOREIGN PATENT DOCUMENTS

| | | |
|---|---|---|
| 206999 | 12/1986 | European Pat. Off. . |
| 236272 | 9/1987 | European Pat. Off. . |
| 0341475 | 11/1989 | European Pat. Off. . |
| 341475 | 11/1989 | European Pat. Off. . |
| 2324010 | 1/1975 | Germany . |

OTHER PUBLICATIONS

Tom Lin, "The Pesticide Manual" (10th Ed) (1994) pp. 482–483.

*Primary Examiner*—Allen J. Robinson
*Attorney, Agent, or Firm*—Sprung Kramer Schaefer & Briscoe

[57] ABSTRACT

A novel fungicidal composition comprising a fungicidally effective amount of a combination consisting of
(i) N-[1-(4-chloro-phenyl)-ethyl]-2,2-dichloro-1-ethyl-3-methyl-cyclopropanecarboxamide of the formula

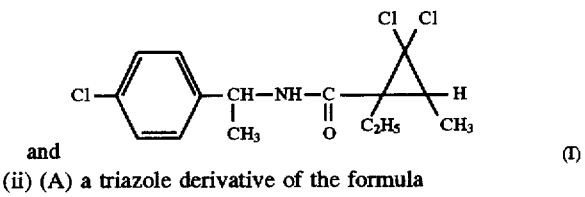

and
(ii) (A) a triazole derivative of the formula

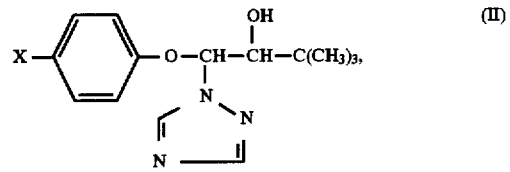

in which X represents chlorine or phenyl, and/or
(B) a pyrrole derivative of the formula

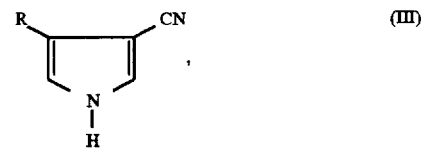

in which R represents

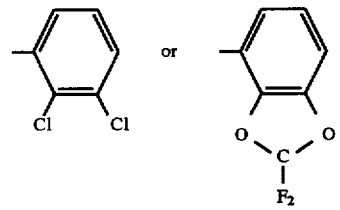

and/or
(C) the imidazole derivative of the formula

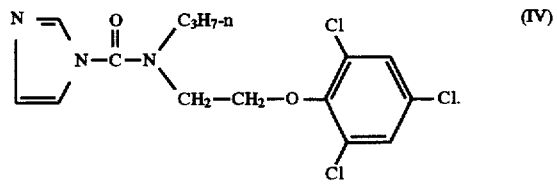

The novel composition shows a synergistic activity.

4 Claims, No Drawings

FUNGICIDAL ACTIVE COMPOUND COMBINATIONS

The present invention relates to novel active compound combinations which consist of the known N-[1-(4-chloro-phenyl)-ethyl]-2,2-dichloro-1-ethyl-3-methyl-cyclopropanecarboxamide, on the one hand, and other known fungicidal active compounds on the other hand, and which are very well suited for controlling phytopathogenic fungi.

It has already been disclosed that N-[1-(4-chloro-phenyl)-ethyl]-2,2-dichloro-1-ethyl-3-methyl-cyclopropanecarboxamide possesses fungicidal properties (cf. EP-A 0 341 475). While the activity of this compound is good, it leaves something to be desired in a number of cases when low application rates are used.

It has furthermore been disclosed that a large number of triazole, imidazole and pyrrole derivatives can be employed for controlling fungi (cf. DE-A-324,010, EP-A 0 206 999, EP-A 0 236 272 and U.S. Pat. No. 3,991,071). However, the effect of these compounds is not always satisfactory, either, when low application rates are used.

It has now been found that the novel active compound combinations consisting of

N-[1-(4-chloro-phenyl)-ethyl]-2,2-dichloro-1-ethyl-3-methyl-cyclopropanecarboxamide of the formula

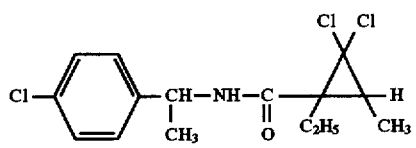

and (A) a triazole derivative of the formula

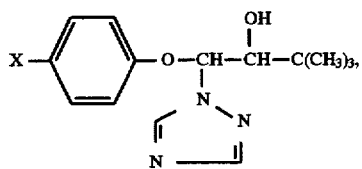

in which X represents chlorine or phenyl, and/or (B) a pyrrole derivative of the formula

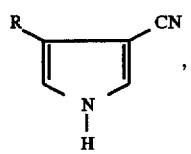

in which R represents

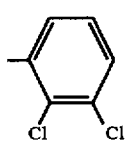 or 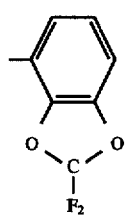

and/or (C) the imidazole derivative of the formula

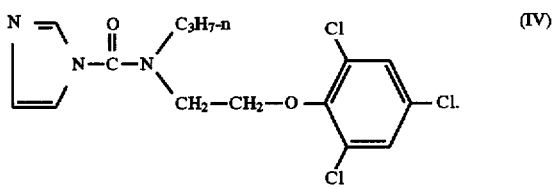

possess very good fungicidal properties.

Surprisingly, the fungicidal effect of the active compound combinations according to the invention is substantially greater than the sum of the effects of the individual active compounds. It is, therefore, a matter of an unforeseeable, genuine synergistic effect and not simply of an addition to the effect.

It is apparent from the structural formula for the active compound of the formula (I) that the compound exhibits three asymmetrically substituted carbon atoms. The product can, therefore, be present as a mixture of different isomers or else in the form of a single component. The compounds N-(R)-[1-(4-chloro-phenyl)-ethyl]-(1S)-2,2-dichloro-1-ethyl-3t-methyl-1r-cyclopropanecarboxamide of the formula

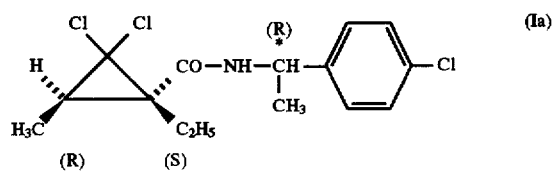

and

N-(R)-[1-(4-chloro-phenyl)-ethyl]-(1R)-2,2-dichloro-1-ethyl-3t-methyl-1r-cyclopropanecarboxamide of the formula

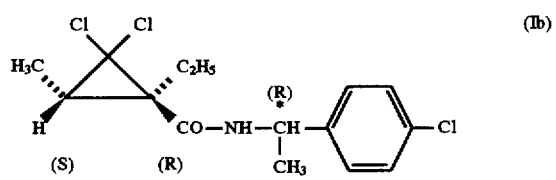

are particularly preferred. The compound of the formula (I) and its individual isomers are known (cf. EP-A 0 341 475).

The formula (II) includes the compounds 1-(4-chlorophenoxy)-3,3-dimethyl-1-(1,2,4-triazol-1-yl)-butan-2-ol of the formula

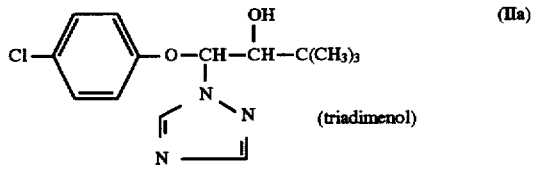

and 1-(4-phenyl-phenoxy)-3,3-dimethyl-1-(1,2,4-triazol-1-yl)-butan-2-ol of the formula

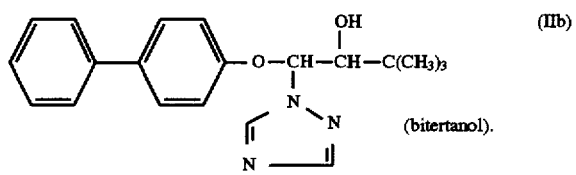

The triazole derivatives of the formula (II) are likewise known (cf. DE-A-2 324010).

The formula (III) includes the compounds
4-(2,3-dichloro-phenyl)-1 H-pyrrole-3-carbonitrile of the formula

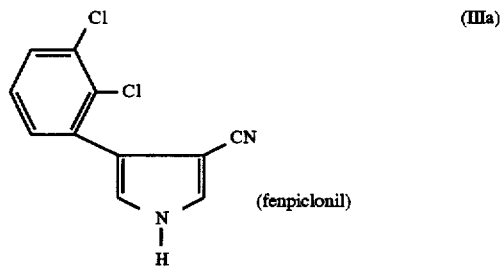

and
4-(2,2-difluoro-1,3-benzodioxol-4-yl)-1 H-pyrrole-3-carbonitrile of the formula

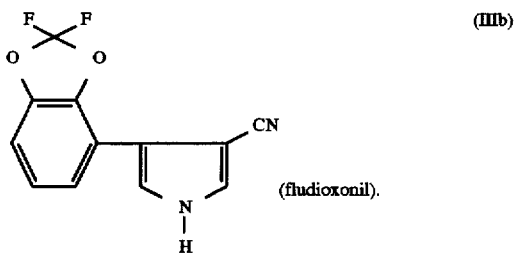

The pyrrole derivatives of the formula (III) are likewise known (cf. EP-A 0 206 999 and EP-A 0 236 272).

The imidazole derivative of the formula (IV) is N-[2-(2,4,6-trichlorophenoxy)ethyl]-N-propyl-1 H-imidazole-1-carboxamide, which is known under the name of prochloraz (cf. U.S. Pat. No. 3,991,071).

In addition to the active compound of the formula (I), the active compound combinations according to the invention contain at least one active compound from the compounds of groups (A) to (C). Over and above this, they may also contain additional, admixed, fungicidally active components.

The synergistic effect is exhibited particularly clearly when the active compounds are present in particular weight ratios in the active compound combinations according to the invention. However, the weight ratios of the active compounds in the active compound combinations may be varied over a relatively wide range. In general, from 0.1 to 10 parts by weight, preferably from 0.2 to 5 parts by weight, of active compounds from groups (A) to (C) are allotted to 1 part by weight of active compound of the formula (I).

The active compound combinations according to the invention possess very good fungicidal properties and can be employed for controlling phytopathogenic fungi such as Plasmodiophoromycetes, Oomycetes, Chytridiomycetes, Zygomycetes, Ascomycetes, Basidiomycetes, Deuteromycetes, etc.

The active compound combinations according to the invention are particularly well suited for controlling Pyricularia, Pellicularia, Cochliobolus, Gibberella, Rhizoctonia and *Fusarium spp.*

The active compound combinations according to the invention may, in particular, be used for controlling fungi on rice and cereals, such as wheat and barley.

The good toleration by plants of the active compound combinations, at the concentrations required for controlling plant diseases, permits treatment of above-ground parts of plants, of vegetative propagation stock and seeds, and of the soil. The active compound combinations according to the invention may be employed for application to leaves or as dressing agents.

The active compounds according to the invention can be converted into the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds or the active compound combinations with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at normal temperature and under atmospheric pressure, for example aerosol propellants, such as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks. As emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products. As dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and plant growth regulators.

The active compound combinations can be used as such or in the form of their formulations or the use forms prepared therefrom, such as ready-to-use solutions, emulsifiable concentrates, emulsions, suspensions, wettable powders, soluble powders and granules. They are used in the customary manner, for example by watering, spraying, atomizing, scattering, spreading, dry seed dressing, wet dressing, liquid dressing, slurry treatment of seeds or encrustation.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The fact that the active compound combinations according to the invention have a good fungicidal effect is evident from the examples which follow. Whereas the individual active compounds exhibit weaknesses in their fungicidal effect, the combinations have an effect which goes beyond a simple summation of effects.

In fungicides, a synergistic effect is always present when the fungicidal effect of the active compound combinations is greater than the sum of the effects of the individually applied active compounds.

EXAMPLE 1

*Cochliobolus sativus* test (barley)/protective

Solvent: 10 parts by weight of N-methyl-pyrrolidone
Emulsifier: 0.6 parts by weight of alkylaryl polyglycol ether To produce a suitable preparation of active compound, 1 part by weight of active compound or active compound combination is mixed with the stated amounts of solvent and emulsifier and the concentrate is diluted with water to the desired concentration.

In order to test for protective activity, young plants are sprayed with the preparation of active compound at the stated application rate.

After the spray coating has dried on, the plants are sprayed with a conidial suspension of *Cochliobolus sativus*.

The plants remain for 48 hours in an incubation cabin at 20° C. and 100% relative atmospheric humidity.

The plants are placed in a greenhouse at a temperature of about 20° C. and a relative atmospheric humidity of about 80%.

Evaluation is effected 7 days after the inoculation. In this test, 0% denotes an efficacy which corresponds to that of the control, whereas an efficacy of 100% denotes that no infestation is observed.

Active compounds, active compound concentrations and experimental results are given in the following table:

TABLE 1

*Cochliobolus sativus* test (barley)/protective

| Active compound | Rate at which active compound applied in g/ha | Efficacy in %, based on the untreated control |
|---|---|---|
| Known | | |
| (Ia/Ib) | 250 | 0 |
| (IIa) (triadimenol) | 250 | 30 |
| According to the invention | | |
| (Ia/Ib) + (IIa) | 125 + 125 | 75 |

EXAMPLE 2

*Gibberella zeae* test (barley)/curative
(Syn. *Fusarium graminearum*)

Solvent: 10 parts by weight of N-methyl-pyrrolidone
Emulsifier: 0.6 parts by weight of alkylaryl polyglycol ether To produce a suitable preparation of active compound, 1 part by weight of active compound or active compound combination is mixed with the stated amounts of solvent and emulsifier and the concentrate is diluted with water to the desired concentration.

In order to test for curative activity, young plants are sprayed with a conidial suspension of *Gibberella zeae*. The plants remain for 24 hours in an incubation cabin at 20° C. and 100% relative atmospheric humidity. The plants are then sprayed with the preparation of active compound at the stated application rate.

After the spray liquor has dried on, the plants remain in a greenhouse under translucent incubation hoods at a temperature of approximately 20° C. and a relative atmospheric humidity of approximately 100%.

Evaluation is effected 4 days after the inoculation. In this test, 0% denotes an efficacy which corresponds to that of the control, whereas an efficacy of 100% denotes that no infestation is observed.

Active compounds, active compound concentrations and experimental results are given in the following table.

TABLE 2

*Gibberella zeae* test (barley)/curative
(Syn. *Fusarium graminearum*)

| Active compound | Rate at which active compound applied in g/ha | Efficacy in %, based on the untreated control |
|---|---|---|
| Known | | |
| (Ia/Ib) | 250 | 13 |
| (IV) (prochloraz) | 250 | 13 |
| According to the invention | | |
| (Ia/Ib) + (IV) | 125 + 125 | 40 |

EXAMPLE 3

*Fusarium nivale* (vat. majus) tea (wheat)/protective
Solvent: 10 parts by weight of N-methyl-pyrrolidone
Emulsifier: 0.6 parts by weight of alkylaryl polyglycol ether To produce a suitable preparation of active compound, 1 part by weight of active compound or active compound combination is mixed with the stated amounts of solvent and emulsifier and the concentrate is diluted with water to the desired concentration.

In order to test for protective activity, young plants are sprayed with the preparation of active compound at the stated application rate.

After the spray coating has dried on, the plants are sprayed with a conidial suspension of *Fusarium nevale* var. majus.

The plants are placed in a greenhouse under translucent incubation hoods at a temperature of approximately 15° C. and a relative atmospheric humidity of approximately 100%.

Evaluation is effected 4 days after the inoculation. In this test, 0% denotes an efficacy which corresponds to that of the control, whereas an efficacy of 100% denotes that no infestation is observed.

Active compounds, active compound concentrations and experimental results are given in the following table.

TABLE 3

*Fusarium nivale* (var. *majus*) test (wheat)/protective

| Active compound | Rate at which active compound applied in g/ha | Efficacy in %, based on the untreated control |
|---|---|---|
| Known | | |
| (Ia/Ib) | 250 | 0 |
| (IIa) triadimenol | 250 | 8 |
| (IIb) bitertanol | 250 | 17 |
| According to the invention | | |
| (Ia/Ib) + } (IIa) | 125 + } 125 | } 42 |
| (Ia/Ib) + } (IIb) | 125 + } 125 | } 50 |

EXAMPLE 4

*Leptosphaeria nodorum* test (wheat)/protective
Solvent: 10 parts by weight of N-methyl-pyrrolidone
Emulsifier: 0.6 parts by weight of alkylaryl polyglycol ether To produce a suitable preparation of active compound, 1 part by weight of active compound or active compound combination is mixed with the stated amounts of solvent and emulsifier and the concentrate is diluted with water to the desired concentration.

In order to test for protective activity, young plants are sprayed with the preparation of active compound at the stated application rate.

After the spray coating has dried on, the plants are sprayed with a suspension of *Leptosphaeria nodorum* spores. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is effected 10 days after the inoculation. In this test, 0% denotes an efficacy which corresponds to that of the control, whereas an efficacy of 100% denotes that no infestation is observed.

Active compounds, active compound concentrations and experimental results are given in the following table.

TABLE 4

*Leptosphaeria nodorum* test (wheat)/protective

| Active compound | Rate at which active compound applied in g/ha | Efficacy in %, based on the untreated control |
|---|---|---|
| Known | | |
| (Ia/Ib) | 250 | 7 |
| | 125 | 0 |
| (IIIa) fenpiclonil | 125 | 7 |
| (IIIb) fludioxonil | 250 | 53 |
| | 125 | 30 |
| According to the invention | | |
| (Ia/Ib) + } (IIIa) | 20.75 + } 104.25 | } 42 |
| (Ia/Ib) + } (IIIb) | 62.5 + } 62.5 | } 65 |
| (Ia/Ib) + } (IIIb) | 208.25 + } 41.75 | } 65 |
| (Ia/Ib) + } (IIIb) | 41.75 + } 208.25 | } 65 |

EXAMPLE 5

*Pyrenophora teres* test (barley)/protective
Solvent: 10 parts by weight of N-methyl-pyrrolidone
Emulsifier: 0.6 parts by weight of alkylaryl polyglycol ether To produce a suitable preparation of active compound, 1 part by weight of active compound or active compound combination is mixed with the stated amounts of solvent and emulsifier and the concentrate is diluted with water to the desired concentration.

In order to test for protective activity, young plants are sprayed with the preparation of active compound at the stated application rate.

After the spray coating has dried on, the plants are sprayed with a conidial suspension of *Pyrenophora teres*.

The plants remain for 48 hours in an incubation cabin at 20° C. and 100% relative atmospheric humidity.

The plants are placed in a greenhouse at a temperature Of about 20° C. and a relative atmospheric humidity of about 80%.

Evaluation is effected 7 days after the inoculation. In this test, 0% denotes an efficacy which corresponds to that of the control, whereas an efficacy of 100% denotes that no infestation is observed.

Active compounds, active compound concentrations and experimental results are given in the following table.

TABLE 5

*Pyrenophora teres* test (barley)/protective

| Active compound | Rate at which active compound applied in g/ha | Efficacy in %, based on the untreated control |
|---|---|---|
| Known | | |
| (Ia/Ib) | 250 | 0 |
| (IIb) bitertanol | 250 | 53 |

TABLE 5-continued

| | Pyrenophora teres test (barley)/protective | |
|---|---|---|
| Active compound | Rate at which active compound applied in g/ha | Efficacy in %, based on the untreated control |
| According to the invention | | |
| (Ia/Ib) + (IIb) | 41.75 + 208.25 } | } 70 |

EXAMPLE 6

Pyrenophora teres test (barley)/curative
Solvent: 10 parts by weight of N-methyl-pyrrolidone
Emulsifier: 0.6 parts by weight of alkylaryl polyglycol ether To produce a suitable preparation of active compound, 1 part by weight of active compound or active compound combination is mixed with the stated amounts of solvent and emulsifier and the concentrate is diluted with water to the desired concentration.

To test for curative activity, young plants are sprayed with a conidial suspension of Pyrenophora teres. The plants remain for 48 hours in an incubation cabin at 20° C. and 100% relative atmospheric humidity. The plants are then sprayed with the active compound preparation at the stated application rate.

The plants are placed in a greenhouse at a temperature of approximately 20° C. and a relative atmospheric humidity of approximately 80%.

Evaluation is effected 7 days after the inoculation. In this test, 0% denotes an efficacy which corresponds to that of the control, whereas an efficacy of 100% denotes that no infestation is observed.

Active compounds, active compound concentrations and experimental results are given in the following table.

TABLE 6

| | Pyrenophora teres test (barley)/curative | |
|---|---|---|
| Active compound | Rate at which active compound applied in g/ha | Efficacy in %, based on the untreated control |
| Known | | |
| (Ia/Ib) | 250 | 18 |
| (IV) prochloraz | 250 | 18 |
| According to the invention | | |
| (Ia/Ib) + (IV) | 41.75 + 208.25 } | } 68 |

EXAMPLE 7

Rhizoctonia solani test (cotton)/seed treatment

The active compounds are used as dry seed dressing agents. They are prepared by extending the relevant active compound or active compound combination with stone meal to form a finely pulverulent mixture which ensures uniform distribution on the seed surface.

For the dressing, the infected seed is shaken for 3 minutes together with the dressing agent in a sealed glass bottle.

2×50 grains of the seed are sown 2 cm deep in a standard soil which is infected with Rhizoctonia solani and are cultivated in a greenhouse at a temperature of approximately 22° C. in seed boxes which are exposed to the light for 15 hours every day.

Evaluation is effected after 8 days. In this test, 0% denotes an efficacy which corresponds to that of the control, whereas an efficacy of 100% denotes that no infestation is observed.

Active compounds, active compound concentrations and experimental results are given in the following table.

TABLE 7

| | Rhizoctonia solani test (cotton)/seed treatment | |
|---|---|---|
| Active compound | Rate at which active compound applied in g/ha | Efficacy in %, based on the untreated control |
| Known | | |
| (Ia/Ib) | 500 | 0 |
| (IV) fludioxonil | 500 | 44 |
| According to the invention | | |
| (Ia/Ib) + (IIIb) | 417 + 83 } | } 47 |
| (Ia/Ib) + (IIb) | 83 + 417 } | } 50 |
| (Ia/Ib) + (IIIb) | 250 + 250 } | } 57 |

EXAMPLE 8

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound or active compound combination is mixed with the stated amount of solvent, and the concentrate is diluted with water and the stated amount of emulsifier to the desired concentration.

To test for protective activity, young rice plants are sprayed with the preparation of active compound until dripping wet. 1 day after the spray coating has dried on, the plants are inoculated with an aqueous spore suspension of Pyricularia oryzae. The plants are then placed in a greenhouse at 100% rel. atmospheric humidity and 25° C.

Evaluation is effected 4 days after the inoculation. In this test, 0% denotes an efficacy which corresponds to that of the control, whereas an efficacy of 100% denotes that no infestation is observed.

Active compounds, active compound concentrations and experimental results are given in the following table.

TABLE 8

| | Pyricularia test (rice)/protective | |
|---|---|---|
| Active compound | Concentration of active compound in the spraying liquid in % | Efficacy in %, based on the untreated control |
| Known | | |
| (Ia/Ib) | 0.01 | 70 |
| | 0.005 | 70 |

TABLE 8-continued

| | Pyricularia test (rice)/protective | |
|---|---|---|
| Active compound | Concentration of active compound in the spraying liquid in % | Efficacy in %, based on the untreated control |
| (IIb) bitertanol | 0.01 | 50 |
| (IIIa) fenpiclonil | 0.005 | 0 |
| (IIIb) fludioxonil According to the invention | 0.005 | 10 |
| (Ia/Ib) + (IIb) | 0.005 + 0.005 | 80 |
| (Ia/Ib) + (IIIa) | 0.0025 + 0.0025 | 80 |
| (Ia/Ib) + (IIIb) | 0.00417 + 0.00083 | 80 |

It is understood that the specification and examples are illustrative but not limitative of the present invention and that other embodiments within the spirit and scope of the invention will suggest themselves to those skilled in the art.

What is claimed is:

1. A synergistic fungicidal composition comprising synergistic fungicidally effective amounts of a combination consisting of (i) N-[1-(4-chloro-phenyl)-ethyl]-2,2-dichloro-1-ethyl-3-methyl-cyclopropanecarboxamide of the formula

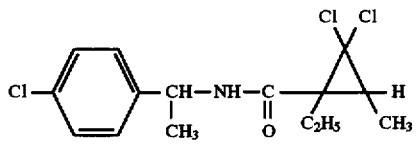
(I)

and (ii) a pyrrole derivative of the formula

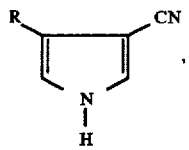
(III)

in which

R represents

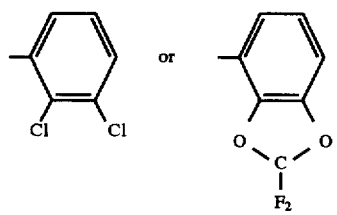

wherein the weight ratio of (i):(ii) is between about 1:0.2 and about 1:5.

2. The synergistic composition according to claim 1, wherein the pyrrole derivative is fludioxonil.

3. The synergistic composition according to claim 1 which comprises synergistic fungicidally effective amounts of a combination consisting of

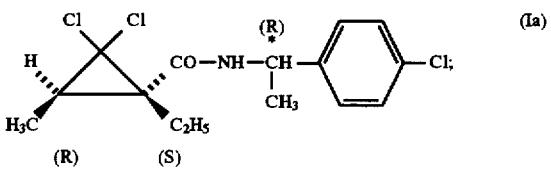
(Ia)

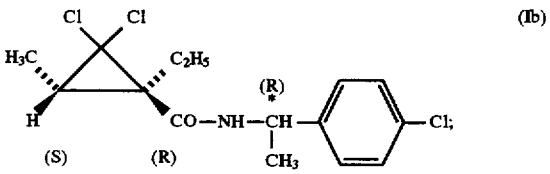
(Ib)

and

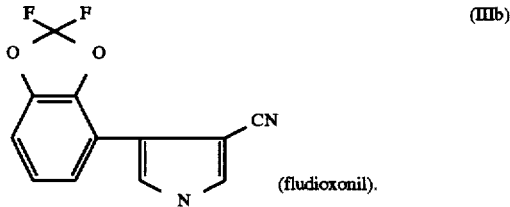
(IIIb) (fludioxonil).

4. A method of combating fungi, which method comprises administering to such fungi or to a fungus habitat a synergistic fungicidally effective amount of a composition according to claim 1.

* * * * *